(12) United States Patent
Makarov et al.

(10) Patent No.: US 7,863,268 B2
(45) Date of Patent: Jan. 4, 2011

(54) BENZOTHIAZINONE DERIVATIVES AND THEIR USE AS ANTIBACTERIAL AGENTS

(75) Inventors: A. Vadim Makarov, Moskow (RU); Stewart T. Cole, Lausanne (CH); Ute Moellmann, Jena (DE)

(73) Assignee: Alere International, Bedfordshire (GB)

( * ) Notice: Subject to any disclaimer, the term of this patent is extended or adjusted under 35 U.S.C. 154(b) by 0 days.

(21) Appl. No.: 12/227,655

(22) PCT Filed: May 24, 2006

(86) PCT No.: PCT/EP2006/004942

§ 371 (c)(1),
(2), (4) Date: Feb. 25, 2009

(87) PCT Pub. No.: WO2007/134625

PCT Pub. Date: Nov. 29, 2007

(65) Prior Publication Data

US 2009/0239851 A1 Sep. 24, 2009

(51) Int. Cl.
C07D 417/06 (2006.01)
A61K 31/541 (2006.01)
(52) U.S. Cl. ............ 514/224.2; 544/6; 544/52
(58) Field of Classification Search ............ 544/6, 544/52; 514/224.2
See application file for complete search history.

(56) References Cited

U.S. PATENT DOCUMENTS 3,522,247 A  7/1970  Cronin et al.

FOREIGN PATENT DOCUMENTS

| AR | 242567 | 4/1993 |
|---|---|---|
| AU | 3704400 | 9/2000 |
| CA | 1322551 | 9/1993 |
| EP | 0245901 | 11/1987 |
| EP | 1568697 | 8/2005 |
| WO | WO 00/51992 | 9/2000 |
| WO | WO 03/042186 | 5/2003 |
| WO | WO 2005/092872 | 10/2005 |
| WO | WO 2007/134625 | 11/2007 |

OTHER PUBLICATIONS

Jan. 1, 2001 Scientific Blueprint for TB Drug Development. The Global Alliance for TB Drug Development, Inc. vol. 81 (Supp. 1) pp. 1-45.
Apr. 2008 "Confronting the scientific obstacles to global control of tuberculosis." Douglas B. Young et al. The Journal of Clinical Investigation. vol. 118, No. 4, pp. 1255-1265.
Apr. 4, 2006 "Synthesis and antileprosy activity of some dialkyldithiocarbamates." Vadim Makarov et al. Journal of Antimicrobial Chemotherapy vol. 57 pp. 1134-1138.
Sep. 10, 2004 "Baterial Persistence as a Phenotypic Switch." Nathalie Q. Balaban et al. Science. vol. 305 pp. 1622-1625.
Sep. 17, 2004 "The Transcriptional Response of *Mycobacterium tuberculosis* to Inhibitors of Metabolism." Helena I. M. Boshoff et al. The Journal of Biological Chemistry vol. 279 pp. 40174-40183.
Jul. 2007 "Microarray Analysis of Whole Genome Expression of Intracellular *Mycobacterium tuberculosis*." Waddell, Simon J. and Philip D. Butcher. Current Molecular Medicine. vol. 7 pp. 287-296.
Jan. 2004 "High content screening applied to large-scale cell biology." Vivek C. Abraham et al. TRENDS in Biotechnology. vol. 22, No. 1, pp. 15-22.
Aug. 27, 2008 "A Fast, Fully Automated Cell Segmentation Algorithm for High-Throughput and High-Content Screening." D. Fenistein et al. Cytometry Part A vol. 73A pp. 958-964.
Dec. 2005 "Decaprenylphosphoryl Arabinofuranose, the Donor of the D-Arabinofuranosyl Residues of Mycobacterial Arabinan, Is Formed via a Two-Step Epimerization of Decaprenylphosphoryl Ribose." Katarina Mikusova et al. Journal of Bacteriology. vol. 187, No. 11, pp. 8020-8025.
Nov. 1995 "Biogenesis of the Mycobacterial Cell Wall and the Site of Action of Ethambutol." Katarina Mikusova et al. Antimicrobial Agents and Chemotherapy. vol. 39, No. 11, pp. 2484-2489.
Sep. 16, 2005 "Deletion of Cg-emb in Corynebacterianeae Leads to a Novel Truncated Cell Wall Arabinogalactan, whereas Inactivation of Cg-ubiA Results in an Arabinan-deficient Mutant with a Cell Wall Galactan Core." Luke J. Alderwick et al. The Journal of Biological Chemistry. vol. 280, No. 37, pp. 32362-32371.
2007 "Targeting the Formation of the Cell Wall Core of *M. tuberculosis*." Clifton E. Barry et al. Infectious Disorders—Drug Targets. vol. 7, No. 2, pp. 182-202.

(Continued)

Primary Examiner—Kahsay T Habte
(74) Attorney, Agent, or Firm—Jordan and Hamburg LLP

(57) ABSTRACT

Disclosed are benzothiazin derivatives of formula (I), preparation methods therefore, and treatment methods employing such compounds as antibacterial agents in treating infectious diseases of mammals caused by bacteria, especially diseases like tuberculosis and leprosy caused by mycobacteria:

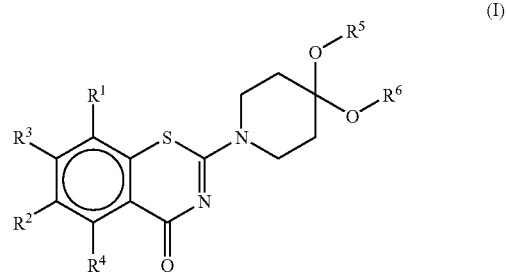

(I)

wherein $R^1$, $R^2$, $R^3$, $R^4$, $R^5$, and $R^6$, and other variables enumerated under one or more of $R^1$, $R^2$, $R^3$, $R^4$, $R^5$, and $R^6$ are as defined.

11 Claims, No Drawings

OTHER PUBLICATIONS

2008 "Biosynthesis of D-arabinose in mycobacteria—a novel bacterial pathway with implications for antimycobacterial therapy." Beata A. Wolucka The FEBS Journal vol. 275 pp. 2691-2711.

May 8, 2009 "Benzothiazinones Kill *Mycobacterium tuberculosis* by Blocking Arabinan Synthesis." Vadim Makarov et al. Science. vol. 324 pp. 801-804.

May 8, 2009 "Benzothiazinones Kill *Mycobacterium tuberculosis* by Blocking Arabinan Synthesis." Vadim Makarov et al. SCIENCE vol. 324 pp. 801-804.

Gheorgiu et al., Abstract of Antituberculous substances, Rev. chim., Acad. Rep. populaire Roumaine 1, No. 1, 958 (1956) XP-002958704.

Zhang, Y. et al. "Mechanisms of Drug Resistance in Mycobacterium tuberculosis" in Tuberculosis and the Tubercle Bacillus (eds. Cole. S. et al.), Chap. 8, pp. 115-140, 2005, ASM Press, Washington, D.C.

BENZOTHIAZINONE DERIVATIVES AND THEIR USE AS ANTIBACTERIAL AGENTS

BACKGROUND OF THE INVENTION

The present invention relates to novel benzothiazin derivatives and their use as antibacterial agents in infectious diseases of mammals (humans and animals) caused by bacteria, especially diseases like tuberculosis (TB) and leprosy caused by mycobacteria.

Thiazinone, their derivatives and their use as antibacterial agents, especially against mycobacteria (TB), laid open for public in AR 24 25 67 A1, AU 37 04 400 A1, CA 13 22 551 C1 or EP 0 245 901 B1 for instance.

As known, there is a threadful worldwide increase in tuberculosis infections with mycobacteria which developed resistance against the available therapeutics (B. R. Bloom, J. L. Murray, tuberculosis: commentary on a reemergent killer. Science 257, 1992, 1055-1064). Extremely dangerous is the development of multidrug resistant (MDR) mycobacteria. These are mycobacteria, resistant at least against two of the most active tuberculosis drugs, isoniazid and rifampicin, but also against streptomycin, pyranzinamid and ethambutol. The proportion of MDR-TB in some countries is already more than 20%. Together with the increased number of TB diseases generally, worldwide it causes about 3,000,000 deaths annually.

For the treatment of such diseases, like (TB) or leprosy there is an urgent need for new drugs with new mechanisms of actions, especially to overcome drug resistance and to overcome the known dramatic side effects of the available drugs.

SUMMARY OF THE INVENTION

The present invention aims at the generation of new compounds with activity against mycobacteria as potential new tuberculosis drugs to overcome problems concerning resistance and drug intolerance.

This aim has been solved by providing compounds of the formula I (I)

Wherein $R^1$ and $R^2$ are, independently each from other, $NO_2$, CN, $CONR^7R^8$, $COOR^9$, CHO, halogen, $NR^7R^8$, $SO_2NR^7R^8$, $SR^9$, $OCF_3$, mono-, di or trifluoromethyl;

$R^3$ and $R^4$ are, independently each from other, H, a saturated or unsaturated, linear or branched aliphatic radical having 1-7 chain members, cycloalkyl having 3-6 carbon atoms, benzyl, $SR^9$, $OR^9$;

$R^5$ and $R^6$ are, independently each from other, a saturated or unsaturated, halogenated or unhalogenated, linear or branched aliphatic radical having 1-8 chain members, cycloalkyl having 3-6 carbon atoms, phenyl, or $R^5$ and $R^6$ together represent a bivalent radical —$(CR^9_2)_m$—, or $R^5$ and $R^6$ together represent bivalent radicals:

wherein m is 1-4, or represent bivalent radicals a saturated or unsaturated mono or polyheterocycles with heteroatoms N, S, O and substituted by $(R^{10})x$, wherein x is 1-4;

$R^7$, $R^8$ and $R^9$ are, independently each from other H or a saturated or unsaturated, halogenated or unhalogenated, linear or branched aliphatic radical having 1-7 chain members, mono-, di or trifluoromethyl, halogen, phenyl, or $R^3$ and $R^4$ together represent a bivalent radical —$(CH_2)_n$— wherein n is 2-7;

$R^{10}$ is H or a saturated or unsaturated, halogenated or unhalogenated, linear or branched aliphatic radical having 1-7 chain members, $NO_2$, $NR^7R^8$, CN, $CONR^7R^8$, $COOR^9$, CHO, halogen, $SO_2NR^7R^8$, $SR^9$, $OR^9$, $OCF_3$, mono-, di or trifluoromethyl, benzyl or phenyl.

In a preferred embodiment the invention concerns compounds of the formula (I) selected from the group consisting of 2-(4-$R^5$-4-$R^6$-piperidin-1-yl)-8-nitro-6-trifluoromethyl-1,3-benzothiazin-4-one, 6-cyano-2-(4-$R^5$-4-$R^6$-piperidin-1-yl)-8-nitro-1,3-benzothiazin-4-one, 6-amido-2-(4-$R^5$-4-$R^6$-piperidin-1-yl)-8-nitro-1,3-benzothiazin-4-one, 2-(1,4-dioxa-8-azaspiro[4.5]dec-8-yl)-8-$R^1$-6-$R^2$-1,3-benzothiazin-4-one, 2-(2-methyl-1,4-dioxa-8-azaspiro[4.5]dec-8-yl)-8-$R^1$-6-$R^2$-1,3-benzothiazin-4-one, 2-[(2R)-2-methyl-1,4-dioxa-8-azaspiro[4.5]dec-8-yl]-8-$R^1$-6-$R^2$-1,3-benzothiazin-4-one, 2-[(2S)-2-methyl-1,4-dioxa-8-azaspiro[4.5]dec-8-yl]-8-$R^1$-6-$R^2$-1,3-benzothiazin-4-one, 2-(2,3-dimethyl-1,4-dioxa-8-azaspiro[4.5]dec-8-yl)-8-$R^1$-6-$R^2$-1,3-benzothiazin-4-one, 2-(1,5-dioxa-9-azaspiro[5.5]undec-9-yl)-8-$R^1$-6-$R^2$-1,3-benzothiazin-4-one, wherein $R^1$, $R^2$, $R^5$ and $R^6$ have the above meanings, The present invention is even more particularly concerned with at least one compound selected from the group consisting of 2-(1,4-dioxa-8-azaspiro[4.5]dec-8-yl)-6,8-dinitro-1,3-benzothiazin-4-one, 2-(2-methyl-1,4-dioxa-8-azaspiro[4.5]dec-8-yl)-6,8-dinitro-1,3-benzothiazin-4-one, 2-(4,4-diethoxypiperidin-1-yl)-6,8-dinitro-1,3-benzothiazin-4-one, 7-methyl-2-(2-methyl-1,4-dioxa-8-azaspiro[4.5]dec-8-yl)-6,8-dinitro-1,3-benzothiazin-4-one, 2-(2-methyl-1,4-dioxa-8-azaspiro[4.5]dec-8-yl)-8-nitro-6-(trifluoromethyl)-1,3-benzothiazin-4-one, 2-(2,3-dimethyl-1,4-dioxa-8-azaspiro[4.5]dec-8-yl)-8-nitro-6-(trifluoromethyl)-1,3-benzothiazin-4-one, 2-(1,5-dioxa-9-azaspiro[5.5]undec-9-yl)-8-nitro-6-(trifluoromethyl)-1,3-benzothiazin-4-one, 2-(1,5-dioxa-9-azaspiro[5.5]undec-9-yl)-8-nitro-4-oxo-1,3-benzothiazine-6-carbonitrile, 2-(2-methyl-1,4-dioxa-8-azaspiro[4.5]dec-8-yl)-8-nitro-4-oxo-1,3-benzothiazine-6-carbonitrile, 8-amino-2-(2-methyl-1,4-dioxa-8-azaspiro[4.5]dec-8-yl)-4-oxo-1,3-benzothiazine-6-carbonitrile and 8-amino-2-(2-methyl-1,4-dioxa-8-azaspiro[4.5]dec-8-yl)-6-(trifluoromethyl)-1,3-benzo-thiazin-4-one.

For the synthesis of the aimed compounds we developed our original method of 1,3-benzothiazin-4-one synthesis with usage of dithiocarbamate derivatives as intermediate (method A). The classical method of 1,3-benzothiazin-4-one synthesis with usage of thiocyanate salts (method B) is usable too. Both are presented in the scheme below.

The compounds of the invention are non-mutagenic at 5 mg/ml in the SOS chromotest.

The compounds of the invention are in vivo therapeutically active in the murine model of tuberculosis infection superior compared to the main antituberculosis drug isoniazid used as a positive control. 100% of mice survived. All control animals died until day 33.

The compound of the invention (especially compound no 2=example 1 in the embodiments), is non toxic after per os administration of doses ranging up to 2000 mg/kg was the compound was well endured by animals in the first and 24 next coming hours after introducing. During 7 days of inves-

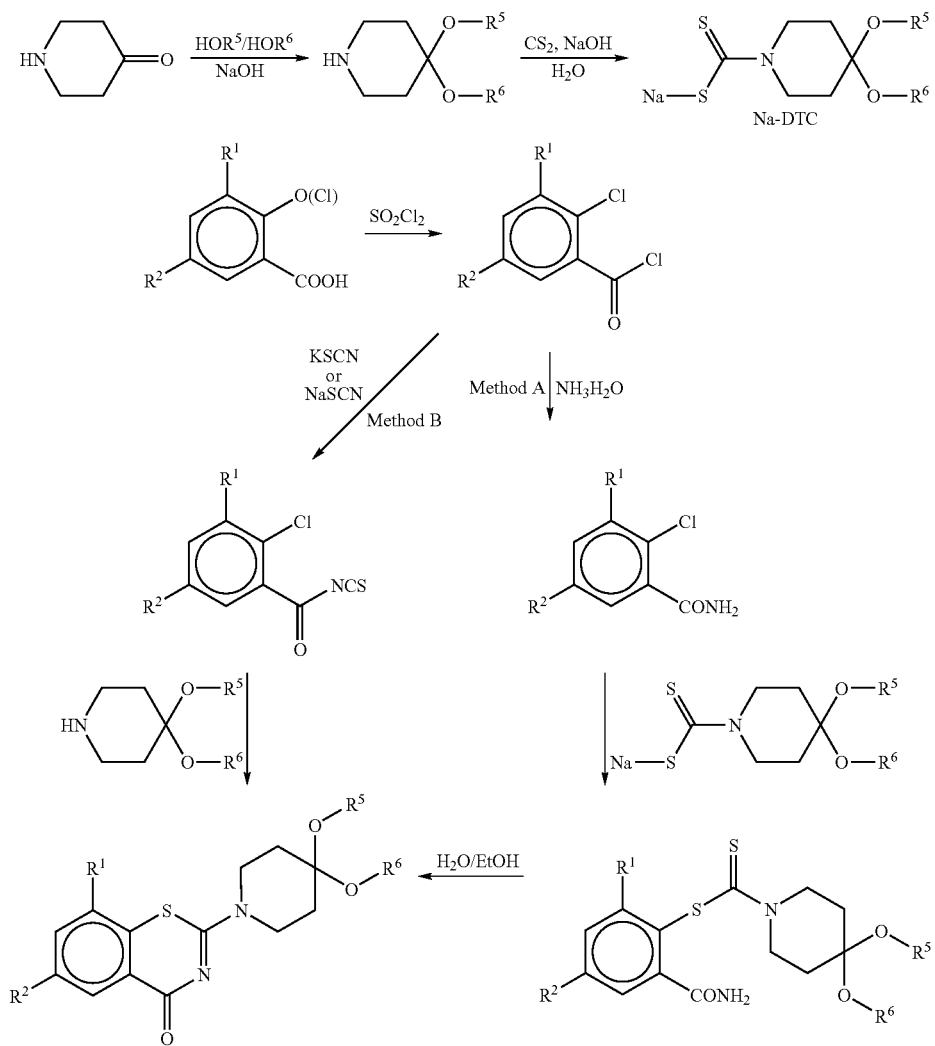

Surprisingly the compounds of the invention exhibit strong antibacterial activity, especially against mycobacteria with minimal inhibitory concentrations (MIC) in the range of 0.23 pg/ml->10 µg/ml for fast growing mycobacteria, of 0.195-1.56 µg/ml for M. tuberculosis, including multiresistant strains determined by the classical method and of 0.030 µg/ml for M. tuberculosis H37Rv determined by the Alamar Blue method. Surprisingly the compounds of the invention demonstrate a high level of selectivity for mycobacteria only which reduces the potential for adverse side effects dramatically.

tigations the compound 2 did not cause changes in general state and behavior of the mice, it did not affect motor and reflex activity, active and calm cycles, grooming, food consumption, there were no cases of animal death. $LD_{50}$ for compound 2 is >2000 mg/kg.

Thus, the compounds of the invention are useful for the treatment of tubercular infection and other mycobacterial infections, in humans and in animals.

Accordingly, the invention concerns pharmaceutical compositions comprising a compound of the formula I.

The invention relates furthermore to a compound of the formula I for use in a method for the treatment of bacterial infections in mammals. Preferred compounds of the formula I for use in such method are those specifically listed above.

The compounds of the invention are formulated for use by preparing a dilute solution or suspension in pharmaceutically acceptable aqueous, organic or aqueous-organic medium for topical or parenteral administration by intravenous, subcutaneous or intramuscular injection, or for intranasal application; or are prepared in tablet, capsule or aqueous suspension form with conventional excipients for oral administration or as suppositorium.

The compounds can be used in dosages from 0.001-1000 mg/kg body weight.

The examples which follow in the subsequent experimental part serve to illustrate the invention but should not be construed as a limitation thereof.

The structures of the compounds of the invention were established by modes of synthesis and elementary analysis, and by nuclear magnetic resonance and/or mass spectra, as well as by X-ray analysis.

DETAILED DESCRIPTION OF THE INVENTION

Starting Materials

Chemicals and solvents were purchased from Lancaster Synthesis (Lancashire, England) or from Aldrich (Sigma-Aldrich Company, St-Louis, US) and were used in the synthesis without additional purification. Melting points were determined according to the BP procedure and are uncorrected (Electrothermal 9001, GB). If analyses are indicated only by the symbols of the elements, analytical results are within ±0.3% of the theoretical values (Carlo-Erba 5500, Italy). NMR spectra were determined with a Varian Unity Plus 400 (USA). Shifts for $^1$H NMR are reported in ppm downfield from TMS ($\delta$). Mass spectra were obtained using a Finnigan SSQ-700 (USA) instrument with direct inject. Reactions and purity of compounds were controlled by TLC with usage Silicagel 60 $F_{254}$ aluminium sheets (Merck Co, Germany).

Example 1

2-(1,4-dioxa-8-azaspiro[4.5]dec-8-yl)-8-nitro-6-(trifluoromethyl)-1,3-benzothiazin-4-one, (compound 1)

Method A.

To a stirred 50 mL solution of 25% aqueous ammonia was added drop-wise a solution of 5 g of 2-chloro-3-nitro-5-trifluoromethylbenzoyl chloride (D. E Welch, R. R. Baron, B. A. Burton, J. Med. Chem. 12; 2; 1969; 299-303) in acetonitrile (10 mL) at −20° C. 10 min later, 50 ml of ethyl acetate was added. The organic phase was separated, washed twice in water, dried over $Na_2SO_4$, treated by activated carbon, filtered and concentrated in vacum. The crude product was purified by crystallization from ethanol. The yield of 2-chloro-3-nitro-5-(trifluoromethyl)benzamide was 92%. mp 195-197° C. (methanol).

Anal. Calcd. for $C_8H_4ClF_3N_2O_3$: C, 35.78; H, 1.50; N, 10.43

Found: C, 36.01; H, 1.53; N, 10.39

0.5 g of 2,2-chloro-3-nitro-5-(trifluoromethyl)benzamide was dissolved in a 25 ml of ethanol. The reaction mixture was treated with of 0.5 g of 1,4-dioxa-8-azaspiro[4.5]decane-8-carbodithioic acid sodium salt dihydrate (Z. Ge, R. Li, T. Cheng, Synth. Commun., 29, 18, 1999, 3191-3196) and stored for 18 h at room temperature. It was then poured into 50 ml of cooled water and the resulting yellow precipitate was filtered off. Pure final product was obtained after recrystallization twice from ethanol. 2-(Aminocarbonyl)-6-nitro-4-(trifluoromethyl)phenyl-1,4-dioxa-8-azaspiro[4.5]decane-8-carbodithioate is light yellow crystalline solid. Yield 0.47 g %. mp 138-140° C.

Anal. Calcd. for $C_{11}H_{12}N_4O_2S_2$: C, 42.57; H, 3.57; N, 9.31; S, 14.21

Found: C, 42.61; H, 3.67; N, 9.22; S, 14.30

0.4 g of 2-(aminocarbonyl)-6-nitro-4-(trifluoromethyl)phenyl-1,4-dioxa-8-azaspiro[4.5]decane-8-carbodithioate was dissolved in a 25 ml of ethanol. The reaction mixture was treated with of 0.32 g of $Na_2HPO_4 \times 12H_2O$ and refluxed for 6 h. It was then cooled and light yellow precipitate was filtered off and washed by 30 ml methanol. Pure final product was obtained after recrystallization twice from ethanol. 2-(1,4-Dioxa-8-aza-spiro[4.5]dec-8-yl)-8-nitro-6-trifluoromethyl)-1,3-benzothiazin-4-one is light yellow crystalline solid. Yield 0.47 g %. mp 211-212° C.

$R_f$((hexane-acetone; 2/1)-0.35

MS m/z 417 (M$^+$).

$^1$H NMR (DMSO-$d_6$) $\delta$ 8.83 and 8.77 (two 1H, two s, 2CH), 3.80 (8H, broad s, N(CH$_2$CH$_2$)$_2$C), 2.02 (4H, broad s, OCH$_2$CH$_2$O) ppm.

Anal. Calcd. for $C_{16}H_{14}F_3N_3O_5S$: C, 46.04; H, 3.38; N, 10.07; S, 7.68

Found: C, 45.94; H, 3.37; N, 10.09; S, 7.76

Method B. The procedure in detail was the same as described in J. Imrich, P. Kristian, Coll. Czech. Chem. Commun., 47, 1982, 3268-3282; D. Koscik, P. Kristian, J. Gonda, E. Dandarova, Coll. Czech. Chem. Commun., 48, 1983, 3315-3328; D. Koscik, P. Kristian, O. Forgac, Coll. Czech. Chem. Commun., 48, 1983, 3427-3432; T. H. Cronin, H.-J. E. Hess, U.S. Pat. No. 3,522,247. Yield of 2-(1,4-dioxa-8-azaspiro[4.5]dec-8-yl)-8-nitro-6-trifluoromethyl)-1,3-benzothiazin-4-one is 0.21%. The compound is identical by spectroscopical data to the compound synthesized by method A.

Example 2

2-(2-methyl-1,4-dioxa-8-azaspiro[4.5]dec-8-yl)-8-nitro-6-(trifluoro-methyl)-1,3-benzothiazin-4-one, (compound 2)

Following the procedure of Example 1. Light yellow crystalline solid.

Yield 54%. mp 192-3° C.

$R_f$(hexane-acetone; 2/1)-0.30.

MS m/z 431 (M$^+$).

$^1$H NMR (DMSO-$d_6$) $\delta$ 8.81 and 8.77 (two 1H, two s, 2CH), 4.24 (1H, m, CH), 4.11 (1H, m, CH), 4.06 (4H, broad s, N(CH$_2$)$_2$), 3.47 (1H, t, CH), 3.27 (1H, s, CH), 1.80 (4H, broad d, C(CH$_2$)$_2$), 1.23 (3H, d, CH$_3$) ppm.

Anal. Calcd. for $C_{17}H_{16}N_3O_5S$: C, 47.33; H, 3.74; N, 9.74; S, 7.43

Found: C, 47.36; H, 3.80; N, 9.87; S, 7.51

Example 3

2-(1,4-dioxa-8-azaspiro[4.5]dec-8-yl)-6,8-dinitro-1,3-benzothiazin-4-one, (compound 4)

Following the procedure of Example 1 with usage of 2-hydroxy-3,5-dinitrobenzoic acid as starting material. Light yellow crystalline solid.

Yield 43%. mp 271-3° C. (EtOH/DMF).

R$_f$(hexane-acetone; 2/1)-0.25.

MS m/z 394 (M$^+$).

$^1$H NMR (DMSO-d$_6$) δ 9.15 and 9.12 (two 1H, two s, 2CH), 3.86 (8H, broad s, N(CH$_2$CH$_2$)$_2$C), 2.97 (4H, broad s, OCH$_2$CH$_2$O) ppm.

Anal. Calcd. for C$_{15}$H$_{14}$N$_4$O$_7$S: C, 45.68; H, 3.58; N, 14.21; S, 8.13

Found: C, 45.34; H, 3.56; N, 14.30; S, 7.98

Example 4

2-(2-methyl-1,4-dioxa-8-azaspiro[4.5]decyl)-6,8-dinitro-1,3-benzothiazin-4-one, (compound 4)

Following the procedure of Example 1 with usage of 2-hydroxy-3,5-dinitrobenzoic acid as starting material. Yellow crystalline solid. Yield 57%. mp 139-142° C. (EtOH/DMF).

R$_f$(hexane-acetone; 2/1)-0.50.

MS m/z 408 (M$^+$).

$^1$H NMR (DMSO-d$_6$) δ 9.08 and 9.11 (two 1H, two s, 2CH), 4.23 (1H, m, CH), 4.10 (1H, m, CH), 4.06 (4H, broad s, N(CH$_2$)$_2$), 3.43 (1H, t, CH), 3.27 (1H, s, CH), 1.80 (4H, broad d, C(CH$_2$)$_2$), 1.20 (3H, d, CH$_3$) ppm.

Anal. Calcd. for C$_{16}$H$_{16}$N$_4$O$_7$S: C, 47.06; H, 3.95; N, 13.72; S, 7.85

Found: C, 46.87; H, 3.91; N, 13.57; S, 7.83

Example 5

2-(2,3-dimethyl-1,4-dioxa-8-azaspiro[4.5]dec-8-yl)-8-nitro-6-(trifluoromethyl)-1,3-benzothiazin-4-one, (compound 5)

Following the procedure of Example 1 with usage of 2-hydroxy-3-nitro-5-trifluoromethylbenzoic acid as starting material. Light yellow crystalline solid. Yield 58%. mp 205-207° C. (EtOH/DMF).

R$_f$(hexane-acetone; 2/1)-0.55.

MS m/z 44522 (M$^+$).

$^1$H NMR (DMSO-d$_6$) δ 8.82 and 8.77 (two 1H, two s, 2CH), 3.86 (4H, broad c, N(CH$_2$)$_2$), 3.45-3.53 (2H, m, 2CH), 2.41 (4H, broad d, C(CH$_2$)$_2$), 1.13-1.17 (6H, m, 2CH$_3$) ppm.

Anal. Calcd. for C$_{18}$H$_{18}$F$_3$N$_3$O$_5$S: C, 48.54; H, 4.07; N, 9.43; S, 7.20

Found: C, 48.66; H, 4.12; N, 9.32; S, 7.46

Example 6

2-(4,4-diethoxypiperidin-1-yl)-6,8-dinitro-1,3-benzothiazin-4-one, (compound 6)

Following the procedure of Example 1 with usage as starting material 2-hydroxy-3,5-dinitrobenzoic acid. Yellow crystalline solid. Yield 32%.

mp 179-181° C. (i-PrOH).

R$_f$(hexane-acetone; 2/1)-0.30.

MS m/z 424 (M$^+$).

$^1$H NMR (DMSO-d$_6$) δ 9.08 and 9.11 (two 1H, two s, 2CH), 3.60-3.67 (4H, m, N(CH$_2$)$_2$) 2.11-2.08 (4H, m, C(CH$_2$)$_2$), 3.47 and 3.57 (two 2H, q, 2OCH$_2$), 1.16 (6H, t, 2CH$_3$), ppm.

Anal. Calcd. for C$_{17}$H$_{20}$N$_4$O$_7$S: C, 48.11; H, 4.75; N, 13.20; S, 7.56

Found: C, 48.12; H, 4.73; N, 13.41; S, 7.67

Example 7

2-(7,12-dioxa-3-azaspiro[5.6]dodec-3-yl)-6,8-dinitro-1,3-benzothiazin-4-one, (compound 7)

Following the procedure of Example 1 with usage as starting material 2-hydroxy-3,5-dinitrobenzoic acid. Yellow crystalline solid. Yield 51%.

mp 193-195° C. (i-PrOH/DMF).

R$_f$(hexane-acetone; 2/1)-0.45.

MS m/z 422 (M$^+$).

$^1$H NMR (DMSO-d$_6$) δ 8.97 and 9.16 (two 1H, two s, 2CH), 3.57-3.74 (8H, m, 4CH$_2$), 1.93-2.35 (8H, m, 4CH$_2$) ppm.

Anal. Calcd. for C$_{17}$H$_{18}$N$_4$O$_7$S: C, 48.34; H, 4.30; N, 13.26; S, 7.56

Found: C, 48.21; H, 4.43; N, 13.30; S, 7.66

Example 8

2-(1,4-dioxa-8-azaspiro[4.5]dec-8-yl)-7-methyl-6,8-dinitro-1,3-benzothiazin-4-one, (compound 8)

Following the procedure of Example 1 with usage as starting material 2-hydroxy-4-methyl-3,5-dinitrobenzoic acid. Yellow crystalline solid.

Yield 51%. mp 207-210° C. (i-PrOH/DMF).

R$_f$(hexane-acetone; 2/1)-0.30.

MS m/z 408 (M$^+$).

$^1$H NMR (DMSO-d$_6$) δ 8.77 (1H, s, CH), 3.86 (8H, broad s, N(CH$_2$CH$_2$)$_2$C), 2.97 (4H, broad c, OCH$_2$CH$_2$O), 2.79 (3H, s, CH$_3$) ppm.

ppm.

Anal. Calcd. for C$_{16}$H$_{16}$N$_4$O$_7$S: C, 47.06; H, 3.95; N, 13.72; S, 7.85

Found: C, 47.12; H, 4.01; N, 13.69; S, 7.94

Example 9

2-(1,4-dioxa-8-azaspiro[4.5]dec-8-yl)-8-nitro-4-oxo-1,3-benzothiazine-6-carbonitrile, (compound 9)

To a stirred solution of 5 g (19 mmol) 2-hydroxy-5-iodobenzoic acid in 50 ml DMF was added by small portions dry 2.5 g (22 mmol) of CuCN (I). The reaction mixture was refluxed during 5 h, 100 ml of water and 50 ml ethylacetate were added. After it conc. Hydrochloric acid was added up to pH ~3 very carefully under good ventilation. The organic phase was separated, washed twice in water, dried over Na$_2$SO$_4$, treated by activated carbon, filtered and concentrated in vacuum. The crude product was purified by crystallization from water. The yield of 5-cyano-2-hydroxybenzoic acid was 71%. Following the procedure of Example 1. Yield 44%. mp 217-220° C. (EtOH/DMF).

R$_f$(hexane-acetone; 2/1)-0.50.

MS m/z 374 (M$^+$).

$^1$H NMR (DMSO-d$_6$) δ 8.74 and 8.67 (two 1H, two s, 2CH), 3.41 (8H, broad s, N(CH$_2$CH$_2$)$_2$C), 2.93 (4H, broad s, OCH$_2$CH$_2$O) ppm.

Anal. Calcd. for C$_{16}$H$_{14}$N$_4$O$_5$S: C, 51.33; H, 3.77; N, 14.97; S, 8.57

Found: C, 51.30; H, 3.84; N, 14.89; S, 8.62

Example 10

2-(2-methyl-1,4-dioxa-8-azaspiro[4.5]dec-8-yl)-8-nitro-4-oxo-1,3-benzothiazine-6-carbonitrile, (compound 10)

Following the procedure of Example 9. Yellow crystalline solid. Yield 34%. mp 251-253° C. (EtOH/DMF).

$R_f$ (hexane-acetone; 2/1)-0.40.

MS m/z 388 (M$^+$).

$^1$H NMR (DMSO-d$_6$) δ 8.73 and 8.61 (two 1H, two s, 2CH), 4.23 (1H, m, CH), 4.11 (1H, m, CH), 4.07 (4H, broad s, N(CH$_2$)$_2$), 3.51 (1H, t, CH), 3.27 (1H, s, CH), 1.81 (4H, broad d, C(CH$_2$)$_2$), 1.22 (3H, d, CH$_3$) ppm ppm.

Anal. Calcd. for C$_{17}$H$_{16}$N$_4$O$_5$S: C, 52.57; H, 4.15; N, 14.43; S, 8.26

Found: C, 52.42; H, 4.08; N, 14.50; S, 8.27

Example 11

2-(1,5-dioxa-9-azaspiro[5.5]undec-9-yl)-8-nitro-4-oxo-1,3-benzothiazine-6-carbonitrile, (compound 11)

Following the procedure of Example 9. Yellow crystalline solid. Yield 40%. mp 230-232° C. (EtOH/DMF).

$R_f$ (hexane-acetone; 2/1)-0.15.

MS m/z 388 (M$^+$).

$^1$H NMR (DMSO-d$_6$) δ 8.74 and 8.61 (two 1H, two s, 2CH), 3.29-3.65 (6H, m, 3CH$_2$), 2.38 (4H, broad s, 2CH$_2$), 1.82-1.93 (4H, m, 2CH$_2$) ppm.

Anal. Calcd. for C$_{17}$H$_{16}$N$_4$O$_5$S: C, 52.57; H, 4.15; N, 14.43; S, 8.26

Found: C, 52.52; H, 4.11; N, 14.59; S, 8.13

Example 12

Determination of the In Vitro Inhibitory Activity of the Compounds of the Invention Against Mycobacteria The antibacterial activities of the compounds against *Mycobacterium smegmatis* SG 987, *M. aureum* SB66, *M. vaccae* IMET 1010670 and *M. fortuitum* B were tested by determination of minimal inhibitory concentrations (MIC) by the micro broth dilution method in Mueller-Hinton broth (Difco) according to the NCCLS guidelines [National Committee for Clinical Laboratory Standards: Methods for dilution antimicrobial susceptibility tests for bacteria that grow aerobically; 5$^{th}$ Ed.; Villanova, Ed.; Approved standard Document M7-A5. NCCLS, (2000)]

Activity against *M. tuberculosis* H37Rv was tested by the following method for determination of minimal inhibitory concentrations (MIC) and minimal bactericidal concentrations (MBC):

Strains were inoculated onto solid Lowenstein-Jensen medium. After 21 days, the cultures grown were used to prepare an inoculum suspension corresponding to 5×10$^8$ microbial cells/ml). With 0.2 ml of that suspension tubes with 2 ml liquid Shkolnikova medium, containing corresponding concentrations of compounds under study—from 100.0 to 0.195 Mg/ml, were inoculated. After 14 days of incubation at 37° C. the tubes with liquid medium were centrifuged for 15 min. at 3000 RPM.

After discarding the supernatant, the sediment was resuspended in 0.8 ml of sterile 0.9% NaCl. 0.1 ml of the suspension was used to prepare smears subsequently stained by the Ziehl-Neelsen method. The remaining sediment was inoculated in 0.2 ml volumes into three tubes with solid drug free Lowenstein-Jensen medium to determine minimal bactericidal concentrations (MBC). The results were read after 21-28 days of cultivation at 37° C. Controls were tubes cultured with test-strains not treated with the studied agents.

Minimal bactericidal concentration of drugs (MBC) was considered as the drug concentration completely inhibiting the growth of mycobacteria on the solid medium. The bacteriostatic effect (MIC) was characterized by the presence of only individual mycobacteria in the smear and a strong decrease in the number of colonies grown on solid media compared to the controls.

The results are presented in Tables 1 and 2.

TABLE 1

Antimicrobial activity of compounds as of the formula I determined by minimal inhibitory concentrations MIC [μg/ml]

| Compound. | *M. smegmatis* | *M. vaccae* | *M. fortuitum* |
| --- | --- | --- | --- |
| 1 | 12.5 ng/ml | 3.12 ng/ml | 12.5 ng/ml |
| 2 | 1.56 ng/ml | 0.76 pg/ml | 0.023 pg/ml |
| 3 | 0.2 μg/ml | 0.0015 μg/ml | 0.006 μg/ml |
| 4 | 0.2 μg/ml | 0.003 μg/ml | 0.003 μg/ml |
| 5 | 6.25 ng/ml | 0.078 ng/ml | 0.078 ng/ml |
| 6 | >10 μg/ml | 0.04 μg/ml | 0.08 μg/ml |
| 7 | 0.78 μg/ml | 0.003 μg/ml | 0.003 μg/ml |
| 8 | 0.4 μg/ml | 0.025 μg/ml | 0.025 μg/ml |
| 9 | 0.05 μg/ml | 3.12 ng/ml | 25 ng/ml |
| 10 | 25 ng/ml | 3.12 ng/ml | 12.5 ng/ml |
| 11 | 0.05 μg/ml | 6.25 ng/ml | 25 ng/ml |

TABLE 2

Antimicrobial activity of compounds of the formula I against Mycobacterium tuberculosis H37Rv and clinical isolates 6341 and 6374 as determined by minimal inhibitory concentrations (MIC) and minimal bactericidal concentrations (MBC)

| Strain | Compound | MBC (μg/mL) | MIC (μg/mL) | MBC (μg/mL) mean | MIC (μg/mL) mean |
| --- | --- | --- | --- | --- | --- |
| H37Rv | 10 | 0.58 | 0.39 | 0.71 | 0.45 |
| 6341 | | 0.78 | 0.58 | | |
| 6374 | | 0.78 | 0.39 | | |
| H37Rv | 9 | 0.29 | 0.195 | 0.75 | 0.52 |
| 6341 | | 1.17 | 0.78 | | |
| 6374 | | 0.78 | 0.58 | | |
| H37Rv | 2 | 0.58 | 0.39 | 0.45 | 0.29 |
| 6341 | | 0.39 | 0.29 | | |
| 6374 | | 0.39 | 0.195 | | |
| H37Rv | 5 | 0.58 | 0.39 | 0.45 | 0.39 |
| 6341 | | 0.39 | <0.39 | | |
| 6374 | | 0.39 | <0.39 | | |
| H37Rv | 1 | 0.58 | 0.39 | 1.75 | 1.17 |
| 6341 | | 2.34 | 1.56 | | |
| 6374 | | 2.34 | 1.56 | | |
| H37Rv | Isoniazid (INH) | 1.15 | 0.97 | 1.15 | 0.97 |
| 6341 | | >100 | >100 | Not active, >100 | |
| 6374 | | >100 | >100 | Not active, >100 | |

Example 13

Determination of the In Vivo Inhibitory Activity of the Compounds of the Invention Against *Mycobacterium tuberculosis* in the Murine TB Model To determine the chemotherapeutic efficacy we used BALB/c line mice with experimental hematogenously disseminated tuberculosis. The mice were obtained from the Central Animal Nursery of the Russian Academy of Medical Sciences. In this study we included mice after quarantine, standardized by weight (20-25 g) and male only. The mice were infected with a 2-week virulent culture of *Mycobacterium tuberculosis* H37Rv by intravenous injection (into tail vein) of the mycobacterial suspension at a dose of $5 \times 10^6$ CFU (Colony Forming Unit) in 0.5 ml saline. All the experimental animals were divided into groups depending on the treatment regimen used (Table 3). Tested drug doses were selected based on the data from literature and on results of previous investigations.

TABLE 3

| No group | Compound | Dose (mg/kg) | Number of animals per group |
|---|---|---|---|
| 3 | 2 | 12 | 10 |
| 4 | 2 | 25 | 10 |
| 5 | Isoniazid (INH) | 25 | 10 |
| 6 | without treatment | | 10 |

Treatment was started the next day after infection. The drugs were introduced orally as suspension in carboxymethylcellulose/water with a small quantity PEG-400.

Chemotherapy was administered daily 6 times per week (except Sunday).

The animals were killed with ether narcosis. To determine the efficacy of each treatment regimen we registered macroscopical changes in parenchymal organs of the mice, growth of mycobacteria from pathologic material on solid media, as well as a bacterioscopical index of organ injury. We carried out a qualitative and quantitative analysis of macroscopical changes in the liver, spleen and lungs and calculated an injury index (using a four-score scale).

Macroscopical evaluation of the efficacy of each treatment regimen was expressed in the efficacy index, calculated using a formula.

$$\text{Efficacy index} = 100\% - \frac{\text{Injury index of the studied group}}{\text{Injury index of the control group}} \times 100$$

Microbiological examination included culture for determination of CFU in parenchymal organs. For this purpose, we homogenised the right lung and separately the spleen with 6% sulfuric acid, centrifuged, washed by water and saline. The yield (about 0.5 mL) was diluted by 1.0 mL of saline and homogenised. This suspension (0.5 mL) of test organs was diluted 100 and 1000 times by saline and was distributed on solid Finn-2 medium. The cultures were incubated at 37° C. for 1 months and read weekly starting from day 10. After 28 days CFU's were counted.

Data of macroscopical and microbiological examinations of parenchymal organs of mice which died during the experiment were also considered in the overall assessment of the experimental results which are represented in tables 4-6.

TABLE 4

Indexes of organ injury in mice and treatment efficacy

| Group | Drug | Dose (mg/kg) | Injury index | Efficacy index (%) |
|---|---|---|---|---|
| 3 | Compound 2 | 12 | 2.1 | 44.7 |
| 4 | Compound 2 | 25 | 1.0 | 78 |
| 5 | INH, Isoniazid | 25 | 1.2 | 70.5 |
| 6 | Control | — | 3.8 | — |

TABLE 5

Results of microbiological examination of right lung and spleen of experimental mice (42 days after inoculation of the culture medium)

| Group | Compound | Dose (mg/kg) | right lung Culture, without dilution CFU | spleen Culture, without dilution CFU |
|---|---|---|---|---|
| 3 | 2 | 12 | ~60 | ~60 |
| 4 | 2 | 25 | ~35 | ~35 |
| 5 | INH, Isoniazid | 25 | ~40 | ~40 |
| 6 | Control | — | >120 (total growth) | >120 (total growth) |

TABLE 6

Survival of animals

| Day of Treatment | Group 3 Compound 2 | Group 4 Compound 2 | Group 5 INH | Group 6 Control |
|---|---|---|---|---|
| 1 | 10 | 10 | 10 | 10 |
| 2 | 10 | 10 | 10 | 10 |
| 3 | 10 | 10 | 10 | 10 |
| 4 | 10 | 10 | 10 | 10 |
| 5 | 10 | 10 | 10 | 10 |
| 6 | 10 | 10 | 10 | 10 |
| 7 | 10 | 10 | 10 | 10 |
| 8 | 10 | 10 | 10 | 10 |
| 9 | 10 | 10 | 10 | 10 |
| 10 | 10 | 10 | 10 | 10 |
| 11 | 10 | 10 | 10 | 10 |
| 12 | 10 | 10 | 10 | 10 |
| 13 | 10 | 10 | 10 | 9 |
| 14 | 10 | 10 | 10 | 9 |
| 15 | 10 | 10 | 10 | 9 |
| 16 | 10 | 10 | 10 | 9 |
| 17 | 10 | 10 | 10 | 9 |
| 18 | 10 | 10 | 10 | 9 |
| 19 | 10 | 10 | 10 | 9 |
| 20 | 10 | 10 | 10 | 8 |
| 21 | 10 | 10 | 10 | 8 |
| 22 | 10 | 10 | 10 | 8 |
| 23 | 10 | 10 | 10 | 8 |
| 24 | 10 | 10 | 10 | 8 |
| 25 | 10 | 10 | 10 | 5 |
| 26 | 10 | 10 | 10 | 4 |
| 27 | 100% | 100% | 100% | 40% |

All control animals died until day 33

The invention claimed is:
1. A compound of formula (I)

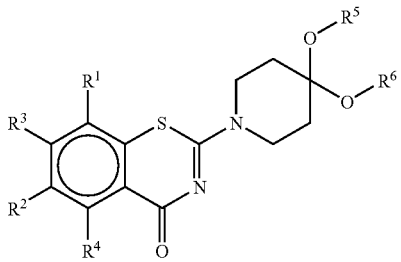

or a salt thereof,
wherein $R^1$ and $R^2$ are, independently, $NO_2$, CN, $CONR^7R^8$, $COOR^9$, CHO, halogen, $SO_2NR^7R^8$, $OCF_3$, or trifluoromethyl;
$R^3$ and $R^4$ are, independently each from other, H, or a methyl group;
$R^5$ and $R^6$ are, independently each from other, a linear or branched aliphatic radical having 1-8 chain members, or $R^5$ and $R^6$ together represent a bivalent radical $-(CR^9{}_2)_m-$, wherein m is 1-4, or $R^5$ and $R^6$ together represent the bivalent radical:

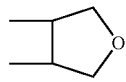

$R^7$, $R^8$ and $R^9$ are, independently H or a linear or branched aliphatic radical having 1-7 chain members, or phenyl.

2. The compound according to formula (I) of claim 1 wherein $R^1$ is $NO_2$, $R^2$ is $CF_3$, $R^3$ and $R^4$ are H, and $R^5$ and $R^6$ have the meanings otherwise given in claim 1.

3. The compound according to formula (I) of claim 1, wherein $R^1$ is $NO_2$, $R^2$ is CN, $R^3$ and $R^4$ are H, and $R^5$ and $R^6$ have the meanings otherwise given in claim 1.

4. The compound according to formula (I) of claim 1, wherein $R^1$ and $R^2$ represents $NO_2$, $R^3$ and $R^4$ are H, and $R^5$ and $R^6$ have the meanings otherwise given in claim 1.

5. A compound selected from the group consisting of:
2-(1,4-dioxa-8-azaspiro[4.5]dec-8-yl)-8-nitro-6-(trifluoromethyl)-1,3-benzothiazin-4-one,
2-(7,12-dioxa-3-azaspiro[5.6]dodec-3-yl)-6,8-dinitro-1,3-benzothiazin-4-one,
2-(1,4-dioxa-8-azaspiro[4.5]dec-8-yl)-7-methyl-6,8-dinitro-1,3-benzothiazin-4-one,
2-(1,4-dioxa-8-azaspiro[4.5]dec-8-yl)-8-nitro-4-oxo-1,3-benzothiazine-6-carbonitrile,
2-(1,4-dioxa-8-azaspiro[4.5]dec-8-yl)-6,8-dinitro-1,3-benzothiazin-4-one,
2-(2-methyl-1,4-dioxa-8-azaspiro[4.5]dec-8-yl)-6,8-dinitro-1,3-benzothiazin-4-one,
2-(4,4-diethoxypiperidin-1-yl)-6,8-dinitro-1,3-benzothiazin-4-one,
7-methyl-2-(2-methyl-1,4-dioxa-8-azaspiro[4.5]dec-8-yl)-6,8-dinitro-1,3-benzothiazin-4-one,
2-(2-methyl-1,4-dioxa-8-azaspiro[4.5]dec-8-yl)-8-nitro-6-(trifluoromethyl)-1,3-benzothiazin-4-one,
2-(2,3-dimethyl-1,4-dioxa-8-azaspiro[4.5]dec-8-yl)-8-nitro-6-(trifluoromethyl)-1,3-benzothiazin-4-one,
2-(1,5-dioxa-9-azaspiro[5.5]undec-9-yl)-8-nitro-6-(trifluoromethyl)-1,3-benzothiazin-4-one,
2-(1,5-dioxa-9-azaspiro[5.5]undec-9-yl)-8-nitro-4-oxo-1,3-benzothiazine-6-carbonitrile,
2-(2-methyl-1,4-dioxa-8-azaspiro[4.5]dec-8-yl)-8-nitro-4-oxo-1,3-benzothiazine-6-carbonitrile.

6. 2-(2-methyl-1,4-dioxa-8-azaspiro[4.5]dec-8-yl)-8-nitro-6-(trifluoromethyl)-1,3-benzothiazin-4-one.

7. The compound of formula I according to claim 1, wherein $R^5$ and $R^6$ are, independently, C1 to C8 alkyl groups.

8. A pharmaceutical composition comprising a compound of the formula I according to claim 1.

9. A method of treating tuberculosis in a mammal, comprising administering to the mammal an effective amount of a pharmaceutical composition comprising a compound of formula (I)

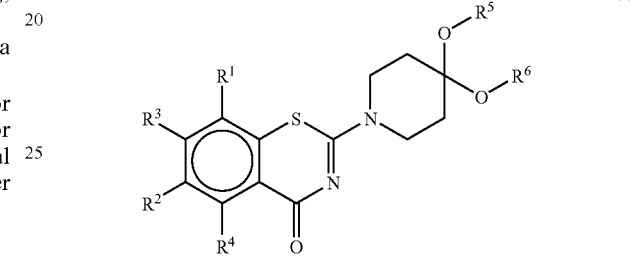

wherein $R^1$ and $R^2$ are, independently, $NO_2$, CN, $CONR^7R^8$, $COOR^9$, CHO, halogen, $SO_2NR^7R^8$, $OCF_3$, or trifluoromethyl;
$R^3$ and $R^4$ are, independently, H or a methyl group
$R^5$ and $R^6$ are, independently, a linear or branched aliphatic radical having 1-8 chain members, or $R^5$ and $R^6$ together represent a bivalent radical $-(CR^9{}_2)_m-$, wherein m is 1-4, or $R^5$ and $R^6$ together represent the bivalent radical:

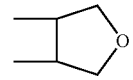

$R^7$, $R^8$ and $R^9$ are, independently H or a linear or branched aliphatic radical having 1-7 chain members, or phenyl.

10. A method for the treatment of a disease selected from tuberculosis and leprosy in a mammal comprising the step of administering to a mammal in need of such treatment an effective amount of the compound of any one of claims 2, 3, 4, 5, or 6.

11. A process for the preparation of a compound according to formula (I) of claim 1 comprising the step of:
treating a compound of the following formula:

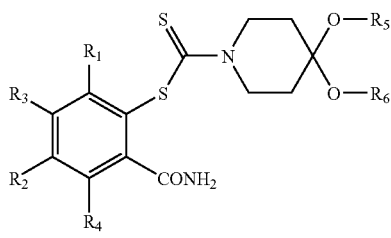

with a mixture of ethanol and water to obtain the compound of formula (I), wherein $R^3$ and $R^4$ are hydrogen, $R^1$ and $R^2$ are, independently, $NO_2$, CN, $CONR^7R^8$, $COOR^9$, CHO, halogen, $SO_2NR^7R^8$, $OCF_3$, or trifluoromethyl;

$R^5$ and $R^6$ are, independently, a linear or branched aliphatic radical having 1-8 chain members, $R^5$ and $R^6$ together represent a bivalent radical —$(CR^9{}_2)_m$—, wherein m is 1-4, or $R^5$ and $R^6$ together represent the bivalent radical

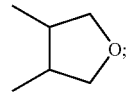

wherein $R^7$, $R^8$, and $R^9$ are, independently, H, phenyl, or a linear or branched aliphatic radical having 1-7 chain members.

* * * * *